United States Patent [19]
Taussig

[11] Patent Number: 5,261,416
[45] Date of Patent: Nov. 16, 1993

[54] SEALED CATHETER DEVICE

[76] Inventor: Lynn M. Taussig, 48, Raffles House, 67 Brampton Grove, London NW4 4BU, England

[21] Appl. No.: 912,141

[22] Filed: Jul. 10, 1992

[51] Int. Cl.$^5$ .............................................. A61B 10/00
[52] U.S. Cl. .................................... 128/759; 604/167
[58] Field of Search ............... 128/749, 752, 758, 759, 128/764, 765; 604/167, 171, 173, 280

[56] References Cited

U.S. PATENT DOCUMENTS

| | | | |
|---|---|---|---|
| 3,894,540 | 7/1975 | Bonner | 604/171 |
| 4,014,333 | 3/1977 | McIntyre | 604/167 |
| 4,023,559 | 5/1977 | Gaskell | 128/759 |
| 4,157,709 | 6/1979 | Schuster et al. | 128/759 |
| 4,324,262 | 4/1982 | Hall | 128/759 |
| 4,457,313 | 7/1984 | Alter | 128/759 |

OTHER PUBLICATIONS

Torres et al., "Diagnostic Value of Quantitative Cultures of Bronchoalveolar Lavage and Telescoping Plugged Catheters in Mechanically Ventilated Patients with Bacterial Pnuemonia", *American Review of Respiratory Disease*, vol. 140, 1989, pp. 306–310.

Marquette et al., "Bronchoscopic Protected Catheter Brush for the Diagnosis of Pulmony Infections", *Chest*, No. 93/4, Apr. 1988, pp. 746–750.

Halperin, et al., "Bacterial Cultures of the Lower Respiratory Tract in Normal Volunteers With and Without Experimental Rhinovirus Infection Using a Plugged Double Catheter System", *American Review of Respiratory Disease*, vol. 125, 1982, pp. 678–680.

Pham et al., "Diagnosis of Nosocomial Pneumonia in Mechanically Ventilated Patients" *American Review of Respiratory Disease*, vol. 143, 1991, pp. 1055–1061.

Cattaneo et al., "Selective Sputum Cultures", *The Journal of Thoracic and Cardiovascular Surgery*, vol. 69, No. 1, Jan. 1975, pp. 152–159.

Zucker et al., "Blind Use of the Double-Lumen Plugged Catheter for Diagnosis of Respiratory Tract Infections in Critically Ill Children", *Critical Care Medicine*, vol. 12, No. 10, Oct., 1984, pp. 867–870.

Ortqvist et al., "Diagnostic Fiberoptic Bronchoscopy and Protected Brush Culture in Patients with Community-Acquired Pneumonia", *Chest*, No. 97/3, Mar., 1990, pp. 576–582.

Joshi et al., "A Comparative Evaluation of Two Fiberoptic Bronchoscopy Catheters: the Plugged Telescoping Catheter Versus the Single Sheathed Nonplugged Catheter", *American Review of Respiratory Disease*, vol. 126, 1982, pp. 860–863.

L. Faling, "A Tale of Two Brushes", *Chest*, No. 79/2, Feb., 1981, pp. 156–156.

Teague et al., "The Use of Quantitative Sterile Brush Culture and Gram Stain Analysis in the Diagnosis of Lower Respiratory Tract Infection", *Chest*, No. 79/2, Feb., 1981, pp. 157–166.

Winterbauer et al., "The Use of Quantitative Cultures and Antibody Coating of Bacteria to Diagnose Bacterial Pheumonia by Fiberoptic Bronchoscopy", *American Review of Respiratory Disease*, vol. 128, 1983, pp. 98–103.

Hayes et al., "Evaluation of Two Bronchofiberscopic Methods of Culturing the Lower Respiratory Tract", *American Review of Respiratory Disease*, vol. 122, 1980, pp. 319–323.

(List continued on next page.)

*Primary Examiner*—Max Hindenburg
*Attorney, Agent, or Firm*—Welsh & Katz, Ltd.

[57] ABSTRACT

A catheter device (20) for taking uncontaminated culture specimens from a patient through an orifice includes an outer catheter (22), an inner catheter (23) disposed within the internal passage (33) of the outer catheter (22) and self-sealing valve means (60) located at a distal end of the outer catheter and remotely actuatable via the inner catheter (23) for selectively sealing the proximal end (31) of the outer catheter (22) to prevent contamination of the aperture (49) employed to obtain a specimen by aspiration.

7 Claims, 1 Drawing Sheet

OTHER PUBLICATIONS

Lundgren et al., "Respiratory Mucosal Damage after Brush Biospy—an Experimental Study in Rabbits", *European Journal of Respiratory Diseases*, vol. 64, 1983, pp. 9-23.

Villers et al., "Reliability of the Bronchoscopic Protected Catheter Brush in Intubated and Ventilated Patients", *Chest*, No. 88/4, Oct., 1985, pp. 527-530.

Torizillo et al., "Use of Protected Telescoping Brush System in the Management of Bacterial Pulmonary Infection in Intubated Patients", *Br. J. Dis. Chest*, vol. 79 No. 125, 1985, pp. 125-131.

Rigal et al., "Prospective Evaluation of the Protected Specimen Brush for the Diagnosis of Pulmony Infections in Ventilated Newborns", *Pediatric Pulmonology*, vol. 8, 1990, pp. 268-272.

Kirkpatrick et al., "Quantitative Bacterial Cultures of Bronchoalveolar Lavage Fluids and Protected Brush Catheter Specimens from Normal Subjects", *American Review of Respiratory Disease*, vol. 139, 1989, pp. 546-548.

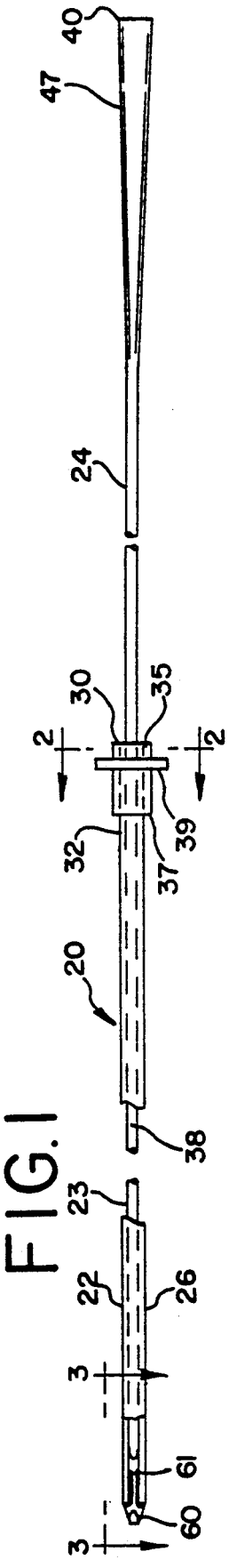
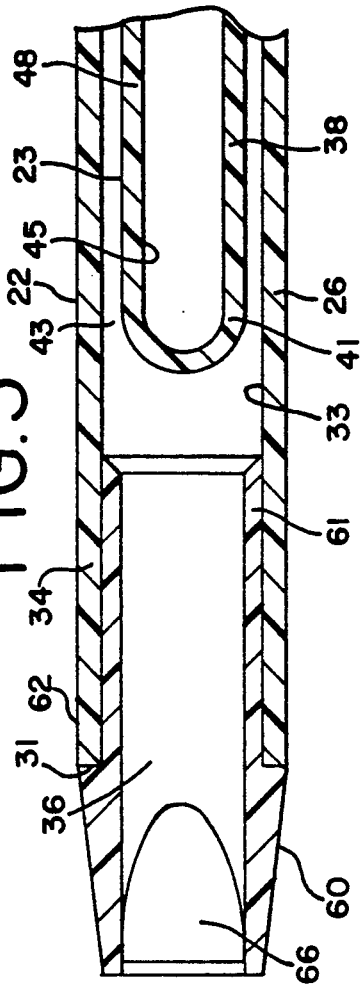
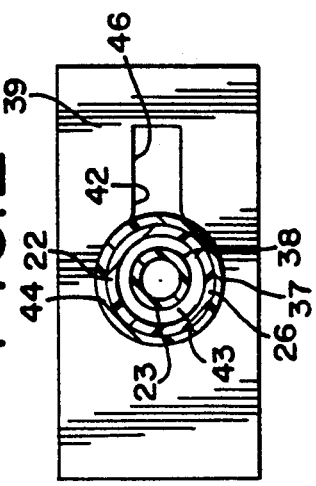
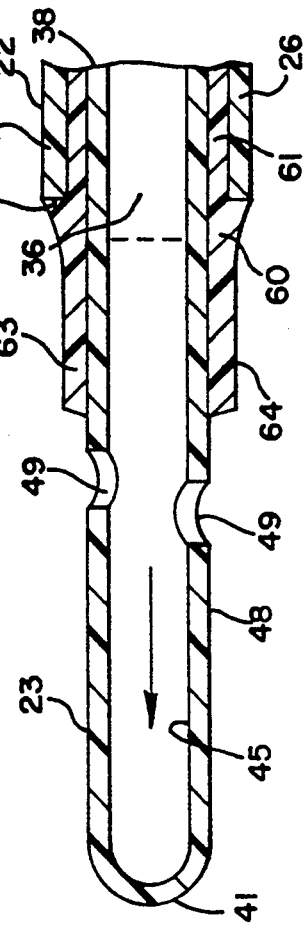
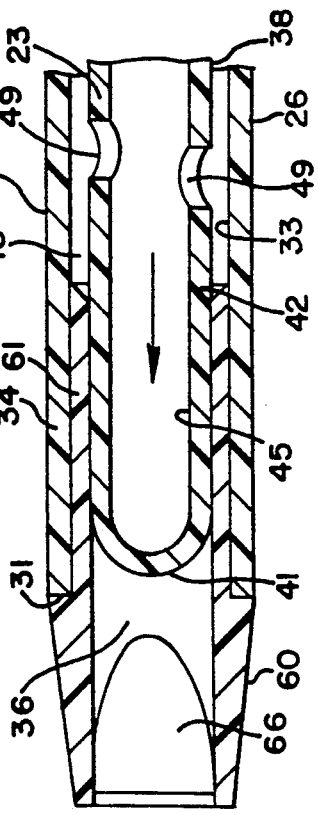

SEALED CATHETER DEVICE

TECHNICAL FIELD

This invention relates generally to a medical device and, more particularly, to a sealed catheter device for obtaining uncontaminated culture specimens.

BACKGROUND ART

Many catheter devices have been designed and patented which can be passed through an orifice of a patient to obtain a culture specimen or tissue sample internally by aspiration or similar method without the necessity of surgical incision. These catheters may be endotracheal catheters, urethral catheters, trocar catheters, or the like, which are employed for withdrawing fluid or tissue from the patient. While not limiting the invention herein, the device disclosed is of a type suitable for obtaining tracheal or sputum specimens from the lower respiratory tract free of contamination from oral, nasal and/or pharyngeal secretions. It should be readily apparent that uncontaminated sampling facilitates accurate diagnosis.

One type of catheter device is shown in Linder et al U.S. Pat. No. 3,957,055 and in Long U.S. Pat. No. 3,867,945 wherein a plastic catheter has an exposed opening at the end thereof to permit the withdrawal of specimens therethrough. No means is provided in this type of catheter to prevent contamination of the sampling catheter as it is inserted through or withdrawn from the patient's orifice.

In another device shown in Kohl U.S. Pat. No. 3,796,221, a pipette having an open-ended tube is employed to remove specimens from various internal locations. Although the pipette is inserted through a sheath, the open end of the sheath itself may contaminate the end of the pipette tube as the tube is moved therethrough.

Results of experiments employing a suction catheter with an inner telescoping catheter are reported in Cattaneo et al., "Selective Sputum Cultures", *Journal of Thoracic and Cardiovascular Surgery* 69 (January 1975): 152-159. The outer catheter has a sealing valve mechanism to minimize contamination of its bore during passage through the nose and pharynx. The valve sealing the distal opening was tripped as the inner catheter was advanced to an exposed position. However, as the inner catheter came through the side of the outer catheter, rather than through the end, the patient's airway was further obstructed resulting in the patient having difficulty respirating.

Khoury, British patent application number 35642/76, filed Aug. 26, 1976, discloses an outer catheter encasing a slidable tubular member which defines a passage through which the inner catheter travels. The slidable member provides means for spacing the passage of the inner catheter away from the inner wall of the outer catheter. The slide-receiving passage is closed by a thin membrane which prevents the inner catheter from becoming contaminated until the membrane is broken by the inner catheter itself, this occurring when the outer catheter is in a position to obtain the desired sample.

SUMMARY OF THE INVENTION

To overcome the problems of the prior art and to provide an inexpensive and reliable method for obtaining uncontaminated culture specimens, a catheter device is constructed with an outer catheter, an inner catheter disposed within the outer catheter and a valve means for selectively sealing the distal end of the outer catheter as the catheter device is inserted into the patient. The valve means is released via the inner catheter to allow the taking of a specimen through a catheter suction opening, which was protected against contamination during insertion.

In a preferred embodiment of the invention, the distal end of the outer catheter is closed by a duckbill valve, although other self-sealing valves could be used. As the inner catheter is extended outward, it engages opposed valve portions and deflects them radially apart. The inner catheter is further advanced to expose the suction opening and allow aspiration of a specimen. As the inner catheter is withdrawn, the duckbill valve closes to seal the distal end of the outer catheter.

BRIEF DESCRIPTION OF THE DRAWINGS

FIG. 1 is an elevational view of a preferred embodiment of a catheter device constructed in accordance with the present invention;

FIG. 2 is a cross-sectional view of the catheter device taken along line 2—2 of FIG. 1;

FIG. 3 is an enlarged fragmentary, longitudinal cross-sectional view of the catheter device taken along the line 3—3 of FIG. 1;

FIG. 4 is an enlarged fragmentary, longitudinal cross-sectional view of the catheter device of FIG. 3 only with the inner catheter advanced toward the valved end of the outer catheter; and FIG. 5 is an enlarged fragmentary, longitudinal cross-sectional view of the catheter device of FIG. 3, only with the inner catheter in extended sample drawing position.

PREFERRED EMBODIMENTS OF THE INVENTION

Referring to FIGS. 1 through 5, an embodiment of the catheter device, generally designated 20, is illustrated and is seen to include an outer catheter 22 and a relatively axially movable inner catheter 23. The outer catheter 22 may be extruded from thermoplastic polyurethane such as Estane, a trademarked product of B. F. Goodrich Co., or other similar material and may have a length of approximately eighteen inches. The inner catheter 23 may be extruded from polypropylene, or other similar material, and may be approximately twenty-five inches in length. External measuring indicia of suitable spacing may be placed on or formed in the inner catheter 23 adjacent the proximal end portion 24 thereof to provide a visual indication at the proximal end of the outer catheter 22 of the axial extension of the distal end of the inner catheter 23 from the distal end of the outer catheter 22.

The outer catheter 22 comprises a tube 26 with a proximal end 30 on a proximal end portion 32 and a distal end 31 on a distal end portion 34. The tube 26 has a longitudinal internal passage 33 defined between the proximal end 30 and the distal end 31, the latter being adapted for insertion into the orifice of a patient. The passage 33 has an axially located opening 35 at the proximal end 30 and an axially located opening 36 at the distal end 31. The proximal end portion 32 has a sleeve 37 encircling and secured to a portion thereof. A clamp plate 39 having a keyhole slot 42 embraces said sleeve 37 with the large end 44 of the key receiving the sleeve 37 urging the clamp plate 39 transverse to the axis of the sleeve 37, squeezes the sleeve 37, outer catheter 22 and inner catheter 23 into the small end 46 of the key to lock the inner catheter 23 and outer catheter 22 together and to cut off flow in the inner catheter 23 while the clamp is on. The distal end portion 34 of the catheter 22 has a duckbill valve 60, formed from silicone rubber or other suitable material, attached thereto.

The duckbill valve 60, one variety of which may be obtained from Moxness Products, Inc. of Racine, Wis., is bonded in place at the end of the outer catheter 22 by suitable elastic adhesive. The duckbill valve 60 has an attaching portion 61 nested in the distal end portion 34 of the catheter 22 with an external shoulder 62 bearing against the end 31 of said catheter. A pair of valve flaps 63 and 64 extend forward of the portion 61 and are urged together at the outer exposed ends to form a slit 65 therebetween. Each flap 63 and 64 has a flat portion 66 on the outer surface thereof diverging from the slit 65, which flat portions 66 serve to facilitate insertion of the catheter device 20 into position.

The inner catheter 23 is centrally disposed within the outer catheter passage 33 and is axially movable relative thereto between a retracted position (FIG. 3) and an extended position axially outward through the slit 65 of the duckbill valve 60 (FIG. 5). The inner catheter 23 comprises a tube 38 having a proximal end 40 on the proximal end portion 47, a distal end 41 on a distal end portion 48, and an internal passageway 45 with one or more side apertures 49 spaced proximally from the distal end 41 and extending through the wall of the tube 38. The inner catheter tube 38 has an external diameter less than the internal diameter of the outer catheter tube 26 to thereby define an annular space 43 therebetween.

When the inner catheter 23 is in an axially withdrawn, retracted position (FIG. 3), the distal end 41 and distal end portion 48 of the inner catheter 23 lies entirely within the outer catheter 22. When the inner catheter 23 is moved axially outward relative to the outer catheter 22, the inner catheter distal end 41 will move into the reduced diametered attaching portion 61 of the duckbill valve 60 (FIG. 4) and will contactingly engage the tapered opposed valve flaps 63 and 64 to deflect the valve flaps radially apart. Thereafter with further axial extension of the inner catheter 23, the apertures 49 will be moved to an exposed position (FIG. 5) to allow the taking of a specimen by aspiration through the passageway 45.

With the inner catheter 23 extended through the duckbill valve 60, the valve flaps 63 and 64 will be flush with or within the diameter of the exterior of the outer catheter 22. Note that the cross-sectional area of the distal end portion 34 of the outer catheter 22 is not increased by exposing the inner catheter 23. This means, contrary to the prior art, that the patient's airway will not be further blocked making respiration even more difficult during the aspiration of the specimen.

By reducing pressure at the apertures 49 which are connected to the suction passageway 45, a specimen may be drawn by aspiration into the apertures 49 for collection. When the inner catheter 23 is retracted, the inherent resiliency of the duckbill valve 60 will effect closure of the valve flaps 63 and 64 to once again seal the interior of the outer catheter 22 and prevent contamination of the inner catheter suction apertures 49.

One application of the catheter device 20 is to take sputum or tracheal aspirate cultures. The catheter is passed through the oropharynx into the trachea. The inner catheter 23 is then passed out of the distal end 31 of the outer catheter 22 and secretions are aspirated into the inner catheter 23 (FIGS. 3 through 5). The inner catheter 23 is then pulled back into the outer catheter 22 and the entire device is removed. The aspirated secretions in the inner catheter 23 can then be cultured and those on the tip of the outer catheter 22 can be semi-quantitatively cultured if desired.

It will be recognized that the implementation of other variations and modifications of the invention in its various aspects will be apparent to those skilled in the art, and that the invention is not limited by the specific embodiments described. It is therefore contemplated to cover by the present invention any and all modifications, variations, or equivalents that fall within the true spirit and scope of the basic underlying principles disclosed and claimed herein.

I claim:

1. A catheter device (20) for obtaining a culture specimen from a patient comprising:

an outer catheter (22) having a longitudinal passage (33) defined between a proximal end (30) and an opening (36) adjacent a distal end (31) thereof, said outer catheter distal end (31) being adapted for insertion into an orifice of the patient;

an inner catheter (23) longitudinally disposed within said passage (33) of said outer catheter (22), said inner catheter (23) having a passageway (45) extending from a proximal end (40) to at least one inner catheter aperture (49) spaced proximally from a distal end (41) thereof and extending through a wall of said inner catheter; and means (60) carried by said distal end (31) of said outer catheter (22) and remotely actuatable via said inner catheter (23) for selectively sealing said opening (36) of said outer catheter (22) to prevent contamination of the at least one aperture (49) in said inner catheter (23) from an external source wherein said means (60) includes a valve having a pair of flap portions (63 and 64) urged together to seal the distal end (31) of the outer catheter (22) wherein said flap portions are adapted to openly extend not further than an outer diameter of said outer catheter.

2. A catheter device (20) of claim 1 wherein said outer catheter opening (36) is through its distal end (31) and said sealing means is a self-sealing valve (60) carried by the distal end (31) of said outer catheter (22) over said outer catheter opening (36), axial extension of said inner catheter (23) through said self-sealing valve (60) positions said inner catheter aperture (49) axially outward from said self-sealing valve (60) to expose said inner catheter aperture (49) and allow the taking of a specimen therethrough.

3. A catheter device (20) as claimed in claim 1 wherein means (39) are provided for securing the outer catheter (22) and inner catheter (23) together against relative axial movement.

4. The catheter device as claimed in claim 1 wherein said flap portions have an outer surface thereof diverging from a slit and said valve includes a reduced diametered attaching portion for attachment inside said outer catheter and an external shoulder for bearing against said distal end of said outer catheter.

5. A catheter device (20) for obtaining a culture specimen from a patient comprising:

an outer catheter (22) having a longitudinal passage (33) defined between a proximal end (30) and a distal end (31) adapted for insertion into an orifice of the patient;

an inner catheter (23) longitudinally disposed within said passage of said outer catheter (22) and axially movable therewithin, said inner catheter (23) having a passageway (45) extending from a proximal end (40) to at least one inner catheter aperture (49) spaced proximally from a distal end (41) thereof and extending through a wall of said inner catheter; and means (60) at the distal end of said catheter device (20) for selectively shielding said inner catheter aperture (49) within said passage (33) of said outer catheter (22) to prevent contamination of said inner catheter aperture (49) from an external source, whereby axial extension of the inner catheter (23) outward positions the inner catheter apertures (49) exteriorly of the outer catheter (22) to allow the taking of a specimen therethrough and axial withdrawal of the inner catheter (23) inward returns the inner catheter aperture (49) to the shielded position in the passage of the outer catheter (22) and wherein said means (60) includes a valve having a pair of flap portions (63 and 64) urged together to seal the distal end (31) of the outer catheter (22) and said flap portions are adapted to openly extend not further than an outer diameter of said outer catheter.

6. A catheter device (20) as claimed in claim 5 wherein means (39) are provided for securing the outer catheter (22) and inner catheter (23) together against relative axial movement.

7. The catheter device as claimed in claim 5 wherein said flap portions have an outer surface thereof diverging from a slit and said valve includes a reduced diametered attaching portion for attachment inside said outer catheter and an external shoulder for bearing against said distal end of said outer catheter.

* * * * *